United States Patent [19]

Slovák

[11] Patent Number: 4,942,880
[45] Date of Patent: Jul. 24, 1990

[54] METHOD FOR NON-INVASIVE ELECTRIC DIAGNOSIS AND THERAPY IN HEMODIALYSIS AND GENERAL MEDICINE

[75] Inventor: Petr Slovák, Praha, Czechoslovakia

[73] Assignee: Ceske vysoke uceni technicke v Praze, Praha, Czechoslovakia

[21] Appl. No.: 211,304

[22] Filed: Jun. 24, 1988

Related U.S. Application Data

[63] Continuation-in-part of Ser. No. 834,917, Feb. 28, 1986, Pat. No. 4,790,319, which is a continuation of Ser. No. 549,487, Nov. 4, 1983, abandoned, which is a continuation-in-part of Ser. No. 343,696, Jan. 28, 1982, abandoned.

[51] Int. Cl.$^5$ ............................................. A61B 5/05
[52] U.S. Cl. .................................................. 128/734
[58] Field of Search ................... 128/419 R, 421, 423, 128/734, 735, 741

[56] References Cited

U.S. PATENT DOCUMENTS

| | | |
|---|---|---|
| 3,320,947 | 5/1967 | Knoll .................................... 128/741 |
| 3,894,532 | 7/1975 | Morey .................................. 128/735 |
| 3,900,020 | 8/1975 | Lock ..................................... 128/422 |
| 3,949,736 | 4/1976 | Vrana et al. . |
| 3,971,365 | 7/1976 | Smith . |
| 3,980,077 | 9/1976 | Shaw . |
| 4,008,712 | 5/1977 | Nyboer . |
| 4,052,978 | 10/1977 | Eugenio ............................... 128/735 |
| 4,233,986 | 11/1980 | Tannenbaum ....................... 128/421 |
| 4,300,574 | 11/1981 | Briggs . |
| 4,301,794 | 11/1981 | Tapper ............................. 128/419 R |
| 4,450,527 | 5/1984 | Sramek ................................ 128/734 |

FOREIGN PATENT DOCUMENTS

| | | |
|---|---|---|
| 1437547 | 5/1976 | United Kingdom . |
| 1559260 | 1/1980 | United Kingdom . |
| 1594724 | 8/1981 | United Kingdom . |

*Primary Examiner*—William E. Kamm
*Attorney, Agent, or Firm*—Klein & Vibber

[57] ABSTRACT

A method of diagnosing and treating abnormal tissue includes the steps of generating an electric signal composed of electrical pulses in the range of 250 Hz to 5 KHz, applying the signal to a patient through two electrodes attached to points on the surface of the patient's body, one point being the treated point, monitoring the average value of current passing through the patient's body; monitoring the rate of change in the average value of the current passing through the patient's body; and determining whether the treated point represents normal tissue or abnormal tissue, based on the rate of change in the average value of the current passing through the patient's body. Treatment of abnormal tissue is continued until the average value of current in a treated point reaches a stable value comparable in magnitude to the average value of the current passing through the patient's body at a point representing normal tissue.

2 Claims, 6 Drawing Sheets

METHOD FOR NON-INVASIVE ELECTRIC DIAGNOSIS AND THERAPY IN HEMODIALYSIS AND GENERAL MEDICINE

This application is a continuation-in-part of application Ser. No. 834,917, filed Feb. 28, 1986, (issued as U.S. Pat. No. 4,790,319 on Dec. 13, 1988) which in turn is a continuation of application Ser. No. 549,487, filed Nov. 4, 1983, now abandoned, which in turn is a continuation-in-part of application Ser. No. 343,696, filed Jan. 28, 1982, now abandoned.

FIELD OF THE INVENTION

This invention relates to a stimulator for hemodialysis, peritoneal dialysis, and for diagnostic and therapeutic use in general medicine.

BACKGROUND OF THE INVENTION

Until now, when treating ailments by means of hemodialysis or peritoneal dialysis, there have been many difficulties, viz. a lengthy process of transmission of metabolic products of the exchange of from intracellular and extracellular spaces into a blood system, in the case of hemodialysis, and a lengthy process of transmission of said products into a dialysis solution, in the case of peritoneal dialysis.

Other complications in hemodialysis and peritoneal dialysis are often polyneuritis, especially with diabetic patients. There may appear spasms of the legs and arms, and trembling, particularly with especially sensitive patients. Many difficulties heretofore encountered are usually obviated by means of chemical remedies. These remedies place an additional load upon the body of the patient who is already ill, and they cause an acceleration of the disruption of the patient's metabolism.

Similar problems may often be encountered in stressed tissue (e.g. in cases of soft tissue injury, ischemia, edemas, muscle contractures etc.) with reduced blood supply and lymphatic drainage and abnormal local metabolic relations. These problems are nowadays treated by various electrotherapeutic methods (TENS, high frequency therapy, lasers, ultrasound, magnetotherapy). These methods do not supply objective information about the state of the treated tissue which could be used for real-time control of the treatment itself. The progress between successive sessions can be judged mostly only from the subjective information supplied by the patient, which poses further problems with determination of effective dosage of the electrotherapy. Without objective diagnostic information it is also difficult to specify exactly the localization of the problem.

SUMMARY OF THE INVENTION

The above drawbacks are obviated by the stimulator for hemodialysis according to the invention. In accordance with the invention the stimulator is provided with at least two electrodes which are to be applied to the patient's body. In a preferred embodiment, at least one of the electrodes is connected to an earphone, then to an instrument measuring or indicating the current $I_{av}$ and its time derivative, the current being supplied thereto by means of a generator. The generator is fed from a direct current supply.

The principal advantage of the invention is in speeding up transmission of metabolic products from the tissue into the blood and lymphatic system. The stimulator thus limits the amount of chemical drugs administered to the patient during dialysis or conventional treatment in general medicine.

The stimulator also speeds up restoration of dynamic balance of metabolic processes when applied transcutaneously to the tissue. These effects are elaborated in the following description which discloses a stimulator and methods for its use.

BRIEF DESCRIPTION OF THE DRAWING

With these and other objects in view, which will become apparent in the following detailed description, the present invention, which is shown by example only, will be clearly understood in connection with the accompanying drawing, in which.

DESCRIPTION OF THE PREFERRED EMBODIMENTS

Figure 1:
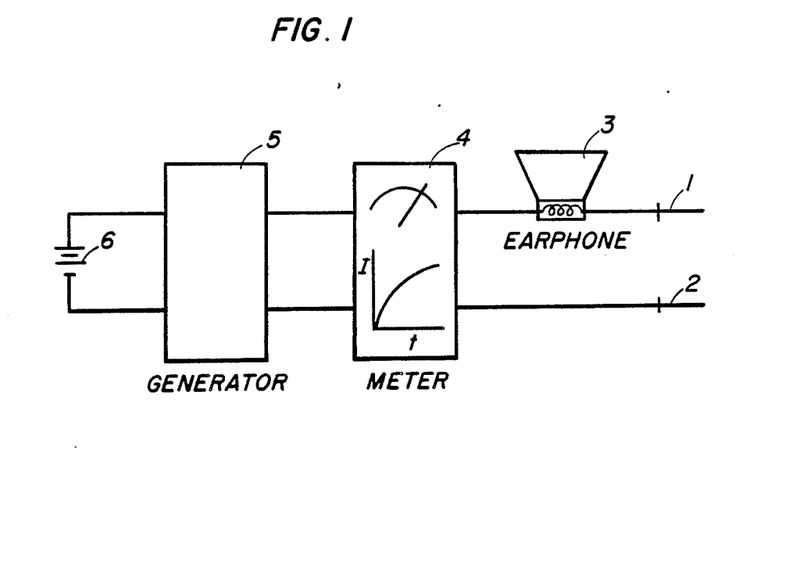
FIG. 1 is a block diagram of a stimulator for hemodialysis.

As shown in FIG. 1, two electrodes 1 and 2 are applied to the body of a patient (not shown) at two different predetermined locations, the electrode 1 being connected through an earphone 3 and through a measuring instrument 4 for measuring the average current and its time derivative supplied thereto from a signal generator 5. Generator 5 is fed from a direct current source 6, shown here as a battery. The electrodes 1 and 2 are made of metallic materials or of electrically conductive polymers. The earphone 3 indicates a conductive connection to the patient's body, and simultaneously, emits audible signals showing the fluctuations of the electric current.

The patient holds e.g. electrode 1 in his hand and electrode 2 is applied to swollen or painful areas or to places with small blood flow or along nerve and lymphatic paths indicated by a doctor (all these points being on the body surface).

The measuring instrument 4 contains an ammeter, shown diagrammatically at the top of FIG. 1, and a current derivative measuring means shown schematically at the bottom of FIG. 1. The measuring instrument may be conventional, provided with an analog output and a digital output for use with other devices, e.g. a programming unit of a hemodialyzing monitor, a plotter/recorder, oscilliscope or the like. Conventional timing and plotting means can be used to graph the average value of current $I_{av}$ against time. For example, the current flowing through the electrodes 1 and 2 can be detected by means of a resistor (not shown). The voltage on this resistor can be transmitted via an optocoupler (not shown) to the input of an integrator (not shown). The signal on its output is proportional to the average current flowing through the resistor. This signal can be led to the input of an A/D converter (not shown) connected to a personal computer with a graphics monitor and a matrix printer (not shown). The computer can be used for recording the data measured using software for plotting Iav and dIav/dt on the monitor screen and copying the graphs on the matrix printer.

Figure 2:
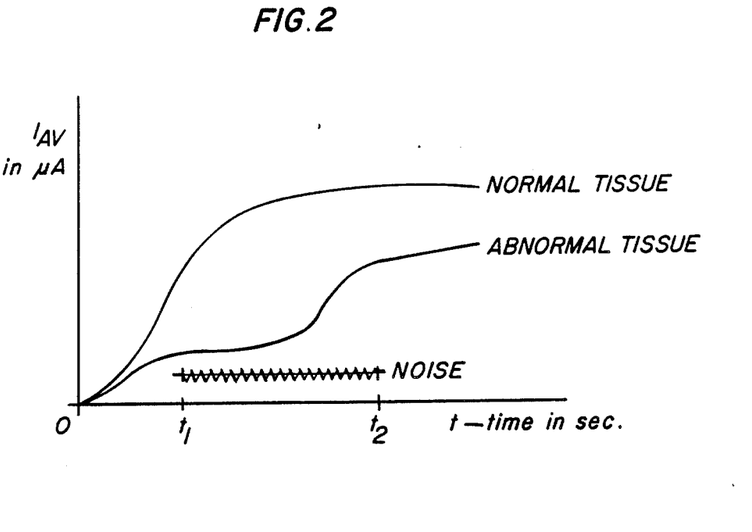
FIG. 2 shows average value of the current $I_{av}$ in normal and abnormal tissue plotted against time of stimulation.

An example of average current $I_{av}$ plotted against time (from the instant of application of electrode 2 to the patient's body) is shown in FIG. 2 illustrating normal tissue and abnormal tissue with local metabolic disturbances.

Small current fluctuations as shown in FIG. 2 (time interval t1-t2) can be detected in abnormal tissue e.g. by noise in earphone 3.

In FIG. 2 it can be seen that in a determined time the differences between normal and abnormal tissues consist not only of the differences between $I_{av}$ values but also of the differences between time derivatives $$\frac{dI_{av}}{dt}.$$

Meter 4 measuring the average value of the current and its time derivative can be realized by usual means, in simplest case by a suitable Deprez D'Arsonval ammeter, which measures directly average value of the current and its time derivative is indicated by meter needle motion velocity. As mentioned above, conventional timing and plotting means can be used to graph a function of current versus time. From this graph, the time derivative of current can be computed either manually, or by conventional electronic computing means. Nevertheless, in many instances, the observed velocity of needle motion of the ammeter is sufficient to establish a rough estimate of the time derivative, being all that is necessary to distinguish normal from abnormal tissue thereby.

The stimulation itself is carried out by consecutively applying electrode 2 to certain points on the skin in an indicated body area. The stimulation is finished when all the points show stable values of current $I_{av}$ comparable in magnitude.

Figure 3:
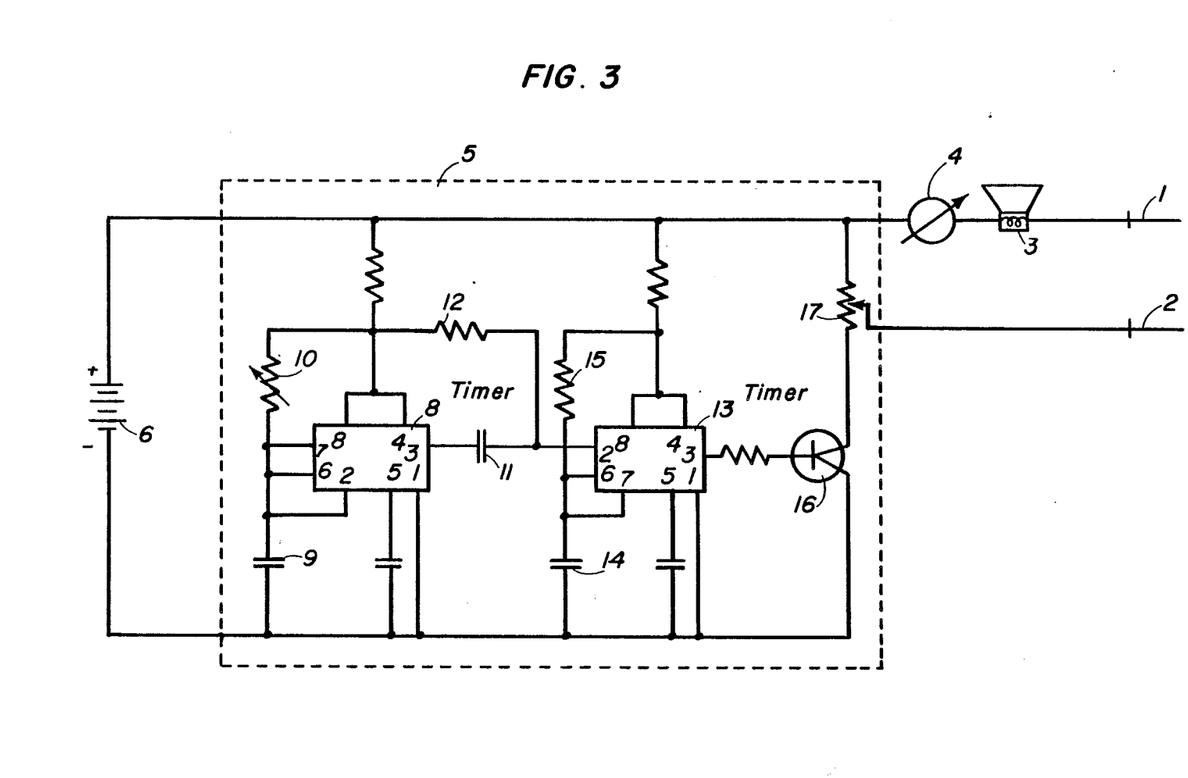
FIG. 3 is a circuit diagram of a preferred embodiment of stimulator in accordance with the invention.
Figure 4A:
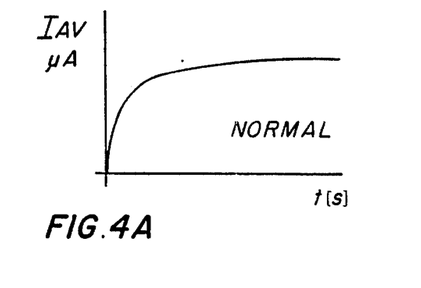
FIGS. 4A through 4E and 4A' through 4E' shows typical examples of current vs. time and current derivative vs. time graphs.
Figure 4B:
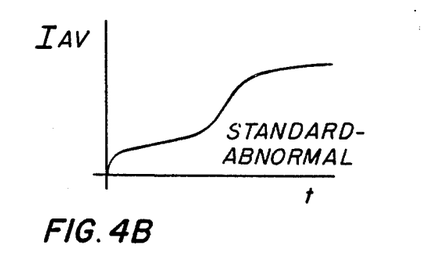
Figure 4C:
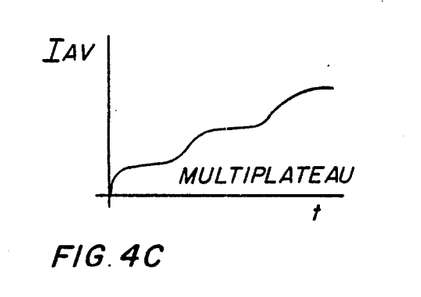
Figure 4D:
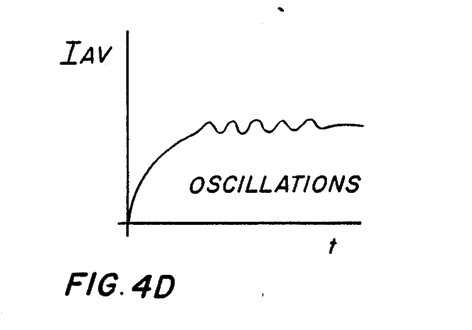
Figure 4E:
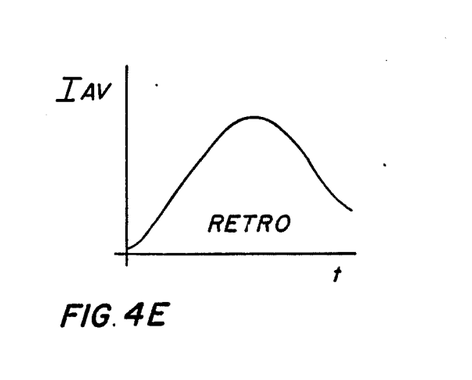

In FIG. 3 an example is shown of a circuit diagram of a simple stimulator.

The generator 5 of the block diagram of FIG. 1 is shown contained within a dash line outline. Generator 5 comprises a first timer 8, type 555, employed in an astable multivibrator. A charging capacitor 9 and an adjustable resistor 10 determine the frequency of the generated electrical pulses. Electrical pulses issue from an output of the timer 8 to an input of a second timer 13 through a derivation unit consisting of a capacitor 11 and a resistor 12. Timer 13, which is also type 555, is connected within the circuit of the monostable multivibrator. The width of the pulse of its output is determined by a capacitor 14 and a resistor 15; advantageously such width is a constant 100 microseconds. A transistor 16 is rendered conductive by pulses from the output of the timer 13. Connected in series with the collector of the transistor 16 is a potentiometer 17, one end of the winding of the potentiometer being connected to main wire 18, whereas the emitter of the transistor 16 is connected to the other main wire 19 of the generator. The sliding contact of the potentiometer 17 is connected e.g. to the electrode 2, and the other output of the potentiometer 17 is connected to the electrode 1 through the earphone 3 and the current measuring instrument 4.

In the above-described arrangement, the stimulator for dialysis operates with rectangular electrical pulses having frequencies in the range of 250 Hz to 5 kHz, such frequency being continuously adjustable by means of a variable resistor 10. The amplitude of the electrical pulses applied to the electrodes 1 and 2 is adjustable in the range of 0 to 17V by means of the potentiometer 17. The battery 6 has an output of 18V. The current measurement range of the measuring instrument 4 is 0 to 300 uA. The velocity of its hand motion indicates the time derivative $$\frac{dI_{av}}{dt}.$$

The earphone 3 is preferably of an electromagnetic type.

Figure 5:
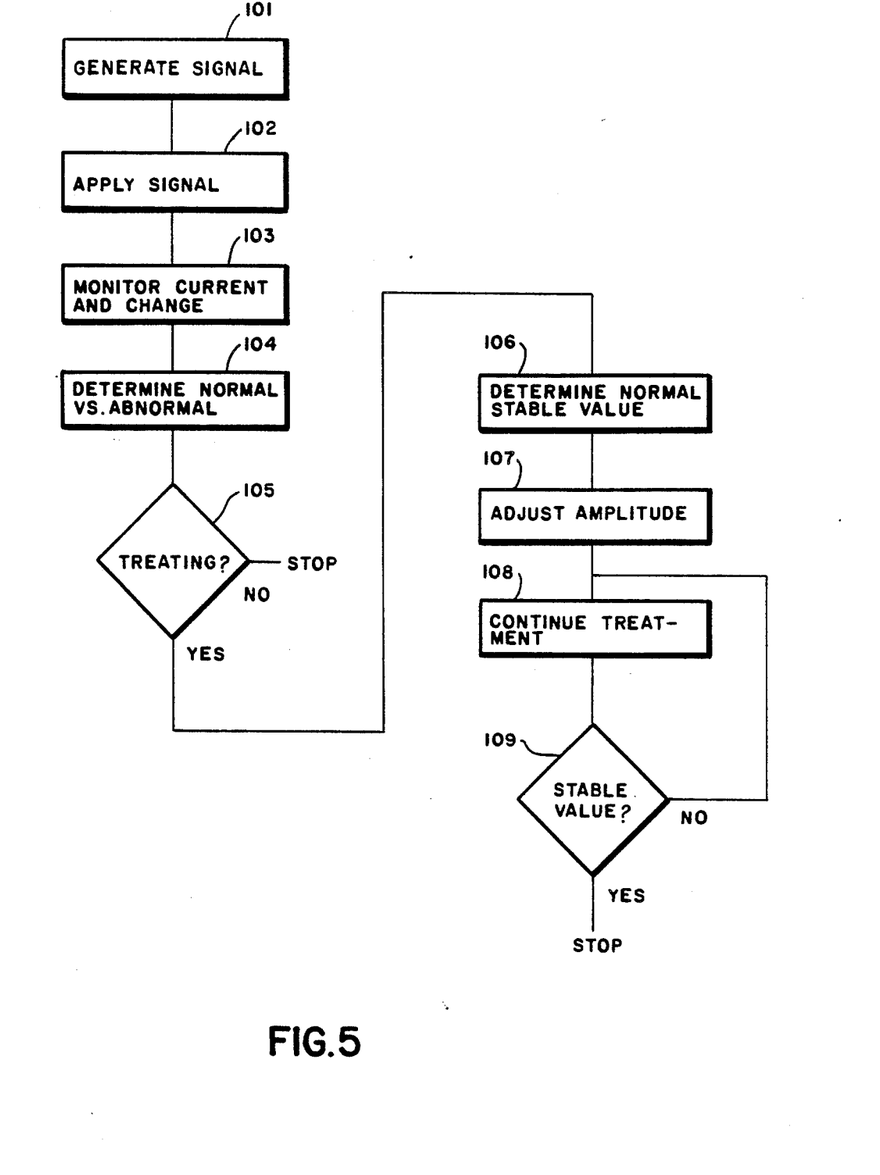
FIG. 5 is a flow chart showing the method of the invention as a series of steps.

Referring generally to FIG. 5, the method of the invention involves generating a signal 101 as discussed at length herein, applying the signal to the patient 102 at preselected points discussed below, and monitoring the change in current 103. After those steps, a determination is made as to the normality of the tissue exposed to the signal 104. If diagnosis is all that is required, the method ends at this point 105. If treatment is desired 105, a normal stable value of current is determined 106, the amplitude of the signal is adjusted to a treating level 107, and treatment continues 108 until a stable value of current is shown 109. Specific examples of the method are discussed below.

For diagnostic and/or therapeutic effects, negative DC rectangular pulses were found to be most convenient for improving capillary blood flow and permeability, lymphatic drainage and local osmotic relations in extracellular spaces, which results in relaxation of the tissue.

The stimulator is basically to be set to a frequency of 3 kHz, peak voltage up to 20 Volts and pulse width 100 microseconds. These "standard" settings are used in most cases such as hemodialysis, physiotherapy and veterinary medicine. The ammeter range is to be selected so that the average current in normal tissue is shown near the maximum of the ammeter dial. The amplitude of the stimulating signal is to be set so that the current can be felt by the patient but remains tolerable.

In cases where analgesia is required, these same settings with reversed polarity (i.e., positive pulses) are to be used.

In case of hemodialysis, the treatment is to be applied applied approximately one hour before hemodialysis.

The whole process of treatment of a patient with the stimulator before dialysis does not take more than 15 minutes.

It is advantageous to repeat the stimulation during hemodialysis or peritoneal dialysis in those spots on the patient's body where the tissue is soaked or where contractions and/or pains appear.

After the dialysis, e.g. after one hour, it is advantageous to carry out the stimulation in areas where painful symptoms appear.

The device according to the invention may also be applied for making diagnoses and for therapy in general medicine. It has been successfully applied e.g., in the following fields:

(1) Facial reconstructive surgery—The current is applied around sutured wounds immediately after removal of dressings. The apparatus is set to 4 kHz and 50 microseconds pulse width. Generally, no more than six treatments in about two weeks are required. If necessary, special liquid contact medium could be used to reduce the pressure of the needle probe. Positive polarity may be used as mentioned above to achieve local analgesia.

(2) Stomatology—The apparatus may be used especially for the treatment of masticatory muscle spasm (non-tetanic trismus). The current is applied in the spiral path centered on temporomandibular joint with point-to-point distance of 7-10 mm. The settings in this case are 3 kHz and 100 microseconds pulse width. Usual exercises are recommended immediately after treatment. Generally about four ten-minute sessions during two weeks are enough.

(3) Surgery—The apparatus may be used especially after major surgery, e.g. thoracotomy or laparotomy. It is to be applied the next day after the operation usually around the sutured wounds with distance between points 15-20 mm. The settings are standard as mentioned above. Generally no more than six sessions in two weeks are required for improving the conditions for healing resulting in decrease of analgetics dosage.

(4) Physiotherapy, Sports Medicine, Repetition Strain Injury—In these areas the relaxation effect may be utilized, e.g. in vertebrogenic and cervicobrachial problems, soft tissue injuries, tennis elbows, ligament injuries. The probe is applied along muscle groups, nerve and lymphatic paths before massage or usual exercises. It may also be used for treatment in extreme painful positions in patients with limited mobility of body parts. This method may be used together with other usual physiotherapeutic methods like laser or ultrasound. The settings are standard as mentioned above. The timetable of the treatment is dependent on the nature of the problem treated (acute, semichronic or chronic problems). Usually no more than twelve sessions are required.

(5) Veterinary Medicine—This method may be used for the treatment of racehorses, especially in cases of tendon or joint problems, muscle contractures or insufficient blood supply of third phalanx. It has also been successfully used for the treatment of injuries in greyhounds, dogs, cats, rabbits. The settings are usually standard and the current is applied anatomically. The timetable depends again on the nature of the problem treated. In these cases, it is useful to record the time-current curves by means of suitable recorder (e.g. computer graphics) for later analysis and evaluation of the progress of the treatment.

The apparatus is also currently being evaluated in other fields, e.g. rheumatology, angiology.

Diagnosis and treatment can be obtained virtually simultaneously as follows: when applying the stimulator to a point, if the current is indicative of normal tissue, stimulation is terminated and a new point is chosen. If the current is indicative of abnormal tissue, stimulation is continued until current stabilizes, and thus treatment of the abnormal tissue is effected.

It is therefore possible to obtain and, if necessary, record objective information from the tissue for the purposes of localization of the area with tissue abnormality and direct control of the treatment in respective points. If recorded, the information may also be used for determining the progress of the treatment between sessions. Typical examples of current vs. time and current derivative vs. time graphs are shown in FIG. 4. These curves characterize local metabolic relations in the tissue. It is supposed that the shapes of the curves may be linked with specific metabolic disorders distinguished by certain electrochemical changes in the tissue which in turn influence the passage of the current from the needle probe through the sweat glands into the soft tissue of the body.

The curves shown in FIG. 4. were recorded by a stimulator with a cylindrical electrode (2) which the patient holds in his hand, while a non-invasive needle probe 1 is being applied to the treated area. This probe has negative polarity.

A curve such as "A" may be found in tissues with normal metabolism. In a slightly traumatized area, a curve such as "B" may be recorded. In injuries with exudate and osmotic disbalances in extracellular spaces, curves such as "C" may be found. In allergic patients, we have found oscillations as shown in "D". In tissues with higher concentrations of uric acid (gout), characteristic curves such as of "E" are recorded.

It is supposed that the function $I_{av}(t)$ reflects the transport of positive ions from the extracellular spaces in the treated area to the negative electrode 1.

For a more sensitive analysis of the movement of charged particles, it is useful to indicate and record the speed of the changes of the current, i.e. the time derivative. These functions are shown as well in FIG. 4 in the right hand column. The analysis of their behaviour can be used for the purposes of computerized recognition of curve shapes and automatic control of the duration of the stimulation in the treated area.

The recorded curves may be also stored in the computer for future references.

In many applications, e.g. sport medicine, a simple deprez meter is quite sufficient for the indication of the current $I_{av}$ and its time derivative (which can be guessed from the speed of the meter needle). The operator can then distinguish normal tissue from abnormal and determine the duration of the stimulation in one point.

Although the invention is described and illustrated with reference to a plurality of embodiments thereof, it is to be expressly understood that it is in no way limited to the disclosure of such preferred embodiments but is capable of numerous modifications within the scope of the appended claims.

I claim:

1. A method of simultaneous diagnosis and treatment of abnormal tissue comprising the steps of
   generating an electric signal composed of electrical pulses in the range of 250 Hz to 5 KHz;
   applying said electric signal to a patient through two electrodes attached to points on the surface of the patient's body, one point being the treated point;
   monitoring the average value of current passing through the patient's body;
   monitoring the rate of change in the average value of the current passing through the patient's body;
   determining whether the treated point represents normal tissue or abnormal tissue, based on the rate of change in the average value of the current passing through the patient's body.

2. A method of treating abnormal tissue comprising the steps of
   generating an electric signal composed of electrical pulses in the range of 250 Hz to 5 KHz;
   applying said electric signal to a patient through two electrodes attached to points on the surface of the patient's body, one point being the treated point;
   monitoring the average value of current passing through the patient's body;
   monitoring the rate of change in the average value of the current passing through the patient's body;

determining whether the treated point represents normal tissue or abnormal tissue, based on the rate of change in the average value of the current passing through the patient's body;

determining a stable average value of current passing through the patient's body at a point representing normal tissue;

adjusting the amplitude of the said electric signal at a point representing normal tissue so that the current is tolerable for the patient;

ending the stimulation in a treated point when the average value of the current reaches a stable value comparable in magnitude to the average value of the current passing through the patient's body at a point representing normal tissue.

* * * * *